United States Patent
Horie et al.

(10) Patent No.: US 6,859,039 B2
(45) Date of Patent: Feb. 22, 2005

(54) DEVICE AND METHOD FOR DETECTING OIL DETERIORATION

(75) Inventors: Kazuyuki Horie, Nagoya (JP); Kiwamu Naito, Chita-gun (JP)

(73) Assignee: Denso Corporation, Kariya (JP)

( * ) Notice: Subject to any disclaimer, the term of this patent is extended or adjusted under 35 U.S.C. 154(b) by 76 days.

(21) Appl. No.: 10/384,069

(22) Filed: Mar. 10, 2003

(65) Prior Publication Data

US 2003/0173970 A1 Sep. 18, 2003

(30) Foreign Application Priority Data

Mar. 8, 2002 (JP) ........................... 2002-064080
Feb. 10, 2003 (JP) ........................... 2003-032794

(51) Int. Cl.[7] .............................................. G01R 27/08
(52) U.S. Cl. .................... 324/438; 324/439; 324/698; 340/438
(58) Field of Search .................. 324/438–450, 324/698, 722, 724; 340/438, 603; 73/53.05, 61.44; 204/421

(56) References Cited

U.S. PATENT DOCUMENTS 5,146,169 A 9/1992 Morishita et al. ........... 324/438
5,523,692 A * 6/1996 Kuroyanagi et al. ........ 324/438
6,549,015 B2 * 4/2003 Horie et al. ................. 324/438

FOREIGN PATENT DOCUMENTS

| JP | 56-47614 | 4/1981 |
| JP | 3-175350 | 7/1991 |
| JP | 4-350552 | 12/1992 |
| JP | 6-201649 | 7/1994 |

* cited by examiner

Primary Examiner—Vincent Q. Nguyen
(74) Attorney, Agent, or Firm—Nixon & Vanderhye P.C.

(57) ABSTRACT

A method and a device for detecting a deterioration of vehicle oil are disclosed in which the end point of the oil service life can be detected with higher accuracy, while at the same time detecting the progress of the oil condition in the vicinity of the end point of the oil service life. The acidity or basicity of the vehicle oil is measured using a pH sensor (11) generating an output in responding to the degree of the acidity or basicity. The deterioration of the vehicle oil can be detected based on the fact that with the increase in vehicle mileage, a line approximating the output of the pH sensor (11) with respect to the vehicle mileage has a tendency to change from a first inclination to a second inclination larger than the first inclination and then from the second inclination to a third inclination smaller than the second inclination.

26 Claims, 5 Drawing Sheets

DEVICE AND METHOD FOR DETECTING
OIL DETERIORATION

BACKGROUND OF THE INVENTION

1. Field of the Invention

The present invention relates to a method and a device for detecting deterioration of automotive vehicle oil, such as engine oil, using a pH sensor which generates an output in response to the degree of the acidity or basicity of the oil, and a method and a device for warning a vehicle user of detected oil deterioration.

2. Description of the Related Art

A conventional pH sensor has been known for detecting the acidity or basicity of an aqueous solution directly and continuously using electrodes. This conventional pH sensor includes a reference electrode presenting a constant electrode potential, and a pH electrode presenting an electrode potential changing in response to the acidity or basicity of the aqueous solution. The pair of electrodes, when immersed in an aqueous solution to be measured, develop a potential difference, substantially proportional to the degree of the acidity or basicity, between them. By measuring this potential difference with a potentiometer built in the sensor, the acidity or basicity of the aqueous solution is detected. Therefore, the dispersion of he electrodes causes different outputs to be generated for the same acidity or basicity of the aqueous solution. In other words, different pH sensors have different output characteristics.

Japanese Unexamined Patent Publication No. 56-47614 discloses an automatic oil changer using the aforementioned pH sensor for detecting the basicity of the engine oil. Further, Japanese Unexamined Patent Publication No. 3-175350 discloses an electrode for improving the reliability of the pH sensor in the oil.

In the device disclosed in the former one of the aforementioned patent publications, the oil is automatically changed when the basicity of the oil decreases to less than a predetermined threshold value. This threshold value is not set by obtaining an output characteristic of the pH sensor with respect to the mileage, i.e. the distance that has been covered by the vehicle. Therefore, the timing of oil change can be affected by output characteristics of the pH sensors. The latter patent publication also deals with electrode materials and a combination thereof but not the output characteristic of the pH sensor with respect to the mileage.

Specifically, in order to prevent engine performance from being deteriorated by sludge (insoluble substance) resulting from oxidization of engine oil, the engine oil contains additives such as an antioxidant and a detergent-dispersant. With the progress of consumption of these additives, the oil comes nearer to the end point of its service life. However, there has been no conventional method or apparatus for detecting the oil deterioration which is capable of detecting the end point of the service life of the oil or the progress of the oil condition in the vicinity of the end point of the service life more accurately, without any influence of output characteristics of the sensors, by monitoring the output characteristic of the pH sensor with respect to the mileage covered by the vehicle to perceive the behavior of the additives in the oil.

Further, Japanese Unexamined Patent Publication No. 6-201649 discloses a device in which the degree of deterioration is judged based on a total acid value map which has been determined for every combination of the electrode materials to be used. However, this device does not judge the degree of deterioration by monitoring a change rate of the output from the pH sensor for the driving mileage or driving time. In addition, Japanese Unexamined Patent Publication No. 4-350552 discloses a device which judges that the oil has deteriorated when the sensor output has changed from a decrease into an increase. However, the device does not judge the deterioration of the oil by detecting a change in the sensor output from a condition of a large change rate into a condition of a small change rate.

SUMMARY OF THE INVENTION

Accordingly, an object of the present invention is to provide an oil deterioration detection method and device capable of detecting an end point of the service life and the behavior in the vicinity of the end point of the service life of a vehicle oil more accurately, and a method and a device for warning the vehicle user of the detected oil deterioration.

Another object of the present invention is to provide an oil deterioration detection method and device capable of detecting an end point of the service life of a vehicle oil by monitoring a relative change in a change rate of an output of a sensor, independently of kinds of oil and a quality of sensors.

According to a first aspect of the present invention, there is provided a method, of detecting a deterioration of vehicle oil, which includes steps of: measuring an acidity or basicity of the vehicle oil using a pH sensor generating an output in response to the degree of the acidity or basicity of the vehicle oil; monitoring a change in a change rate of the output from the pH sensor with one of an increasing driving mileage or driving time of a vehicle; detecting the fact that the output from the pH sensor, after changing from a changing at a first change rate to a changing at a second change rate greater than the first change rate, changes from the changing at the second change rate to a changing at a third change rate greater than the second change rate; and judging that the service life of the vehicle oil has expired when the output from the pH sensor comes to change at the third change rate to detect the deterioration of the vehicle oil.

In the method described above, the service life of the vehicle oil is judged based on a relative change in the change rate of the sensor output which varies with the progress of consumption of the additives in the vehicle oil. As the tendency of the change in the change rate of the sensor output retains a similar pattern, independently of the kinds of oil and the quality of the sensors, the above method of detecting the deterioration of the vehicle oil can detect the end point of the service life of the vehicle oil independently of the kinds of oil or the quality of the sensors.

In a preferred embodiment of the method described above, the monitoring step includes a step of using an approximation line approximating the output from the pH sensor with respect to the mileage of the vehicle, and the method further includes a step of detecting the deterioration of the vehicle oil, based on the fact that the approximation line has a tendency to change from a first inclination to a second inclination lager than the first inclination and from the second inclination to a third inclination smaller than the second inclination, with the increasing mileage of the vehicle.

In the method described above, the oil deterioration is detected based on the output characteristic of the pH sensor of which the output approximation line changes from the first inclination to the second inclination and from the second inclination to the third inclination, with the progress of consumption of the additives in the oil. Thus, the end point of the service life of the oil can be detected with higher accuracy, which enables the progress of the oil condition before the end point of the service life and the expiry of the service life to be detected.

In the preferred embodiment, the judging step may include steps of predetermining a threshold value existing between a portion of the second inclination and a portion of the third inclination in the approximation line, and detecting that the vehicle oil has reached the end point of the service life thereof based on the predetermined threshold value.

The change in the output of the pH sensor from the second inclination to the third inclination is considered to indicate that the additives contained in the oil have been substantially consumed and that sludge is ready to develop, so that the end point of the oil service life apparently exists on a course where the inclination of the approximation line changes from the second inclination to the third inclination. In view of the fact that the arrival at the end point of the oil service life is detected based on a threshold value existing on the course where the approximation line changes from the second inclination to the third inclination, the point at which almost all of the additives in the oil have been consumed can be detected as the end point of the oil service life. Thus, the end point of the oil service life can be detected with higher accuracy.

Preferably, the method described above further includes a step of judging that the vehicle oil has reached about one half of the service life thereof when the approximation line has come to have the second inclination.

The change in output of the pH sensor from the first inclination to the second inclination is considered to indicate that almost all of the antioxidant in the oil has been consumed and the oil is about to be oxidized rapidly. Therefore, it can be judged that the vehicle oil has reached about one half of its service life when the approximation line has come to have the second inclination. Thus, a middle point of the service life can be detected.

Further, in the method described above, the judging step includes a step of judging that the vehicle oil has passed over the end point of its service life when the approximation line has come to have the third inclination.

The change in the output of the pH sensor from the second inclination to the third inclination is considered to indicate that almost all of the additives in the oil have been consumed and that sludge is ready to develop, i.e. that the oil has passed the end point of its service life. Therefore, since it can be judged that the oil has passed the end point of its service life based on the change of the inclination of the approximation line, the expiry of the oil service life can be detected even in the case where the output from the pH sensor fails to increase as usual due to leakage, etc.

In another preferred embodiment of the method described above, the monitoring step includes steps of defining a plane with the driving mileage or driving time as an abscissa thereof and with the output of the pH sensor as an ordinate thereof perpendicular to the abscissa, and using a vector on the plane starting from a point on a coordinate having a driving mileage or driving time $x_0$ and a corresponding output $V_0$ from the pH sensor and ending at a point on a coordinate having a driving mileage or driving time $x_1$ greater than $x_0$ and a corresponding output $V_1$ from said pH sensor. The method further includes a step of detecting the deterioration based on the fact that the inclination of said vector has a tendency to change from a substantially constant or decreasing condition to an increasing condition and from the increasing condition to a substantially constant or decreasing condition, with the increasing driving mileage or driving time.

In this embodiment, the deterioration of the vehicle oil can be detected based on the change in the inclination of the vector obtained from the driving mileage or driving time and the corresponding output of the pH sensor. This inclination of the vector changes in a similar pattern with the increasing driving mileage or driving time, independently of the kinds of oil and the quality of the sensors. Therefore, this embodiment makes it possible to detect the end point of the service life of the vehicle oil, independently of the kinds of oil and the quality of the sensors.

Preferably, in the above embodiment, the output from the pH sensor at first decreases in a predetermined range S of the driving mileage or driving time from a oil exchange and thereafter increases with the increasing driving mileage or driving time, and a point of a minimum output from the pH sensor within the predetermined range S of the driving mileage or driving time from the oil exchange is defined as the starting point.

In this case, as the starting point is clearly defined, the end point of the service life can be detected more correctly.

More preferably, the step of detecting the deterioration of the vehicle oil is performed based on a change in the inclination of the vectors obtained by sampling the outputs of the pH sensor at a regular interval of the driving mileage or driving time in a predetermined range of a recent driving mileage or driving time.

This makes it possible to further reduce the capacity of memory for the pH sensor and consequently its cost, because a range of data required to be stored is limited.

According to a second aspect of the present invention, there is provided a method of detecting a deterioration of vehicle oil, which includes steps of: measuring an acidity or basicity of the vehicle oil using a pH sensor generating an output in response to the degree of the acidity or basicity of the vehicle oil; defining a plane with one of a driving mileage or driving time of the vehicle as one axis and the output from the pH sensor as the other axis perpendicular to the one axis; using a vector on the plane starting from a point on a coordinate having a driving mileage or driving time $x_0$ and a corresponding output $V_0$ from the pH sensor and ending at a point on a coordinate having a driving mileage or driving time $x_1$ greater than $x_0$ and a corresponding output $V_1$ from the pH sensor; monitoring a change in a change rate of the output from the pH sensor; and judging the deterioration of the vehicle oil, based on the fact that the inclination of the vector changes with the increasing driving mileage or driving time.

In the method described above, the change in the change rate of the output from the pH sensor can be easily monitored on based on the change in the inclination of the vector obtained from the driving mileage or driving time and the corresponding output of the pH sensor. As the change rate of the sensor output changes in a similar pattern, independently of kinds of oil and a quality of sensors, the deterioration of the vehicle oil can be detected more precisely, independently of the kinds of oil or the quality of the sensors.

According to a third aspect of the present invention, there is provided a method of warning a vehicle user of the deterioration of the vehicle oil detected by the method described above.

This method enables the warned vehicle user to take appropriate protective measures in response to the warning, for example, by exchanging old oil with new oil.

According to a fourth aspect of the present invention, there is provided a device for detecting a deterioration of a vehicle oil, which includes a pH sensor mounted on an oil pan of the vehicle for generating an output in response to the degree of the acidity or basicity of the vehicle oil; and means connected to the pH sensor for judging the deterioration of the vehicle oil, based on a driving mileage input to the pH sensor and the corresponding output from the pH sensor and in which the judging means detects the fact that the output from the pH sensor, after changing from a changing at a first change rate to a changing at a second change rate greater than the first change rate, changes from the changing at the second change rate to a changing at a third change rate greater than the second change rate, and judges that the service life of the vehicle oil has expired when the output from the pH sensor comes to change at the third change rate.

In a preferred embodiment of the device described above, the judging means detects the deterioration of the vehicle oil, based on the fact that an approximation line approximating the output from the pH sensor with respect to the mileage of the vehicle has a tendency to change from a first inclination to a second inclination larger than the first inclination and from the second inclination to a third inclination smaller than the second inclination, with the increasing mileage of the vehicle.

In the preferred embodiment, the judging means may detect that the vehicle oil has reached the end point of the service life thereof, based on a predetermined threshold value existing between a portion of the second inclination and a portion of the third inclination in the approximation line.

In the device described above, the judging means preferably detects the changing of the approximation line to the second inclination, based on the output from the pH sensor, and judges that the vehicle oil has reached about one half of the service life thereof when the approximation line has come to have the second inclination.

Also, in the device described above, the judging means preferably detects the changing of the approximation line to the third inclination, based on the output from the pH sensor, and judges that the vehicle oil has passed over the end point of the service life when the approximation line has come to have the third inclination.

According to a fifth aspect of the present invention, there is provided an oil deterioration warning device, which includes the deterioration detection device described above; and means for warning a vehicle user of the deterioration of the vehicle oil detected by the deterioration detection device.

BRIEF DESCRIPTION OF THE DRAWINGS

The above and other objects, features and advantages of the present invention will become more apparent from the following description of the preferred embodiments thereof with reference to the accompanying drawings, wherein.

DESCRIPTION OF THE PREFERRED EMBODIMENTS

An embodiment of the present invention will be described below with reference to the accompanying drawings.

Figure 1:
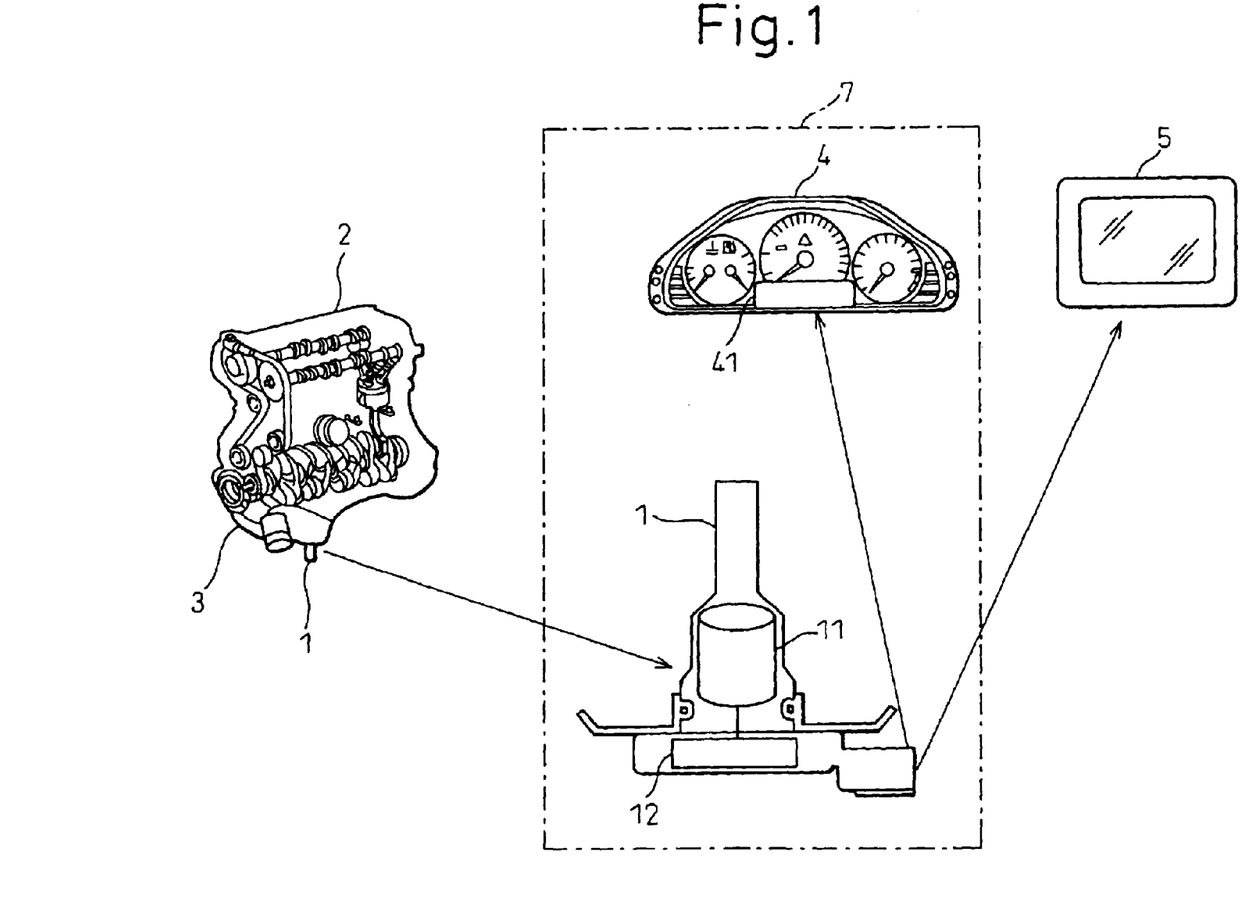
FIG. 1 is a diagram showing a configuration of an embodiment of an oil deterioration warning system including an oil deterioration detection device and an oil deterioration warning device according to the present invention.

As shown in FIG. 1, an oil deterioration detection device (hereinafter referred simply as a detection device) 1 is disposed on an oil pan 3 of an engine portion of an automotive vehicle. The detection device 1 comprises a pH sensor 11 for detecting the acidity or basicity of oil using electrodes, and a microcomputer 12 is connected to the pH sensor 11. The pH sensor 11 outputs a voltage substantially proportional to the degree of the acidity of engine oil which is vehicle oil in the oil pan 3. Specifically, the pH sensor 11 is configured to produce increased output voltage with the increased acidity of oil. The microcomputer 12 functions as means for judging the deterioration of engine oil based on the output voltage from the pH sensor 11.

An oil deterioration warning device (hereinafter referred to simply as a warning device) 7 includes the detection device 1 and an instrument panel 4 connected to the detection device 1. The panel 4 is mounted on the vehicle for indicating the speed, or the like, and includes a display unit 41 for indicating a warning of the detected oil deterioration. Thus, the panel 4 functions as means for warning the vehicle user of the oil deterioration.

Figure 2:
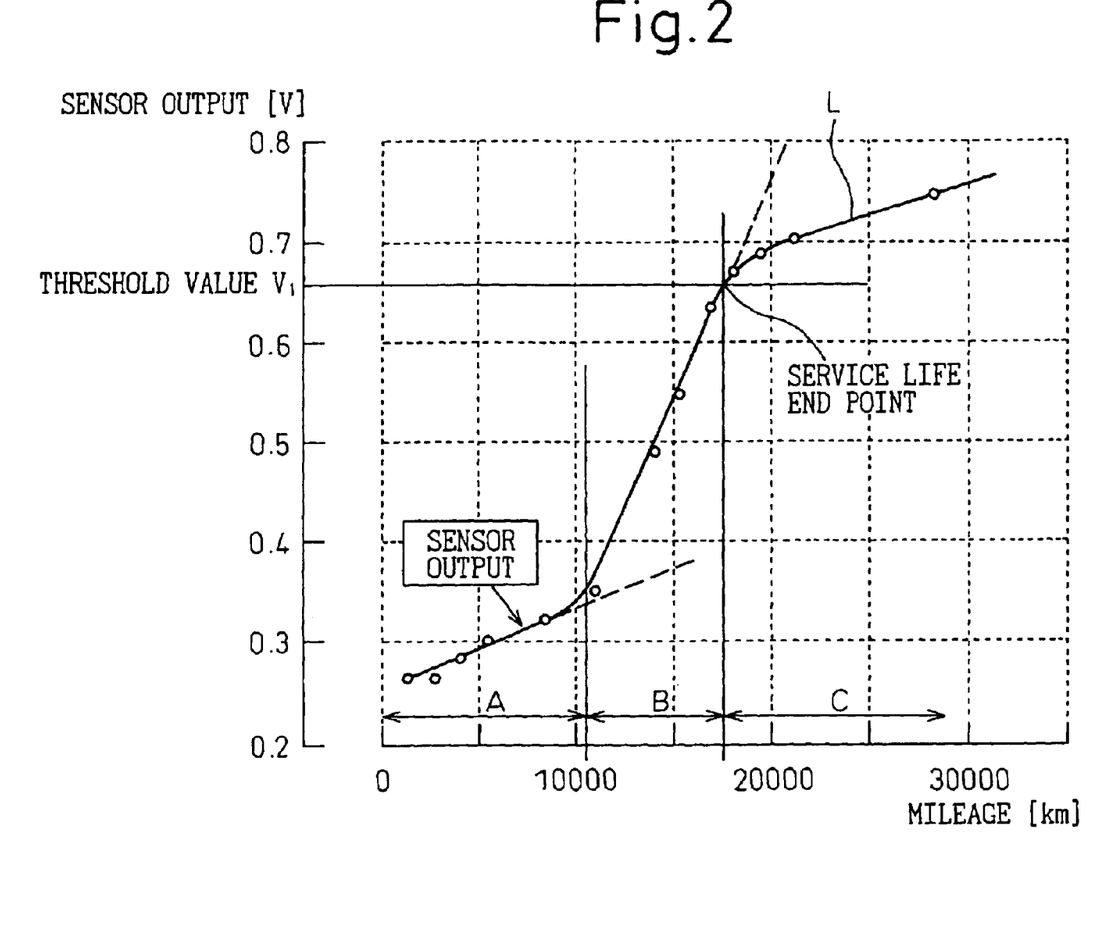
FIG. 2 is a graph showing output characteristics of a pH sensor.

FIG. 2 shows the change in output voltage from the pH sensor 11 in relation to the mileage of the vehicle. In FIG. 2, a line L represents a line approximating the output (indicated by circles in FIG. 2) from the pH sensor 11. As the mileage increases, the line L first rises at a relatively gentle and substantially same inclination (called the first inclination), as shown in an area A of FIG. 2, and then begins to rise sharply at a substantially same inclination (called a second inclination) larger than the first inclination, as shown in an area B of FIG. 2. After that, the line L substantially comes to converge at steady inclination (called a third inclination) smaller than the second inclination, as shown in an area C of FIG. 2. It has been found that the approximation line L has a tendency to change from the second inclination to the third inclination at the mileage about twice as large as the one associated with the change from the first inclination to the second inclination.

The line L is considered to change as shown in FIG. 2 for the following reason.

The engine oil contains an antioxidant and a detergent-dispersant. The antioxidant reduces the peroxides generated from the oil and generates an acid such as sulfuric acid. The detergent-dispersant neutralizes and disperses the acid generated from the antioxidant. Therefore, as long as the antioxidant and the detergent-dispersant are existent, the oxidization of the oil is suppressed, so that the output of the pH sensor 11 rises only gently as shown in the area A.

Then, as the antioxidant is consumed, the oxidization of the oil is greatly promoted. Therefore, the output from the pH sensor 11 rises sharply as shown in the area B.

After that, as the detergent-dispersant is also consumed, sludge comes to be formed in the oil. In the process, the amount of the acid generated from the antioxidant comes to converge due to the consumption of the antioxidant. Therefore, the outputs of the pH sensor 11 assume a gentle curve as shown in the area C and soon reach a stable state.

The rate at which the additives is consumed changes with the running conditions of the vehicle. In the case where the additives are consumed rapidly, the line approximating the output of the pH sensor 11 changes, at the point where the mileage is smaller than for the line L in FIG. 2, from the first inclination to the second inclination and from the second inclination to the third inclination. In the case where the additives is consumed slowly, on the other hand, the approximation line changes, at the point where the mileage is longer than for the line L, from the first inclination to the second inclination and from the second inclination to the third inclination. Nevertheless, the relative tendency, in which the approximation line changes from the first inclination at the beginning of the driving to the second inclination larger than the first inclination and from the second inclination to the third inclination smaller than the second inclination, remains unchanged and is finally followed by a substantially stable state. Also, the output voltage from the pH sensor 11 at the time of changing from the second inclination to the third inclination is not greatly affected by the running conditions of the vehicle and is substantially constant in accordance with the properties of the oil (unless there is no leakage from the pH sensor 11 or the like incident).

As described above, the change in the inclination of the output from the pH sensor 11 can be considered to represent the process of consumption of the additives. Especially, it can be estimated that the end point of the oil service life exits in the area where the output changes from the second inclination to the third inclination. In view of this, after a relation between the mileage of the vehicle and the output voltage from the pH sensor 11 as shown in FIG. 2 is firstly obtained, a voltage value $V_1$ lying between the approximation line of the second inclination and the approximation line of the third inclination is then defined or set as a threshold value. It can be judged that the oil has reached the end point of its service life when the output of the pH sensor 11 reaches the threshold value $V_1$. Also, when the second inclination of the approximation line changes to the third inclination, it can be judged that the service life of the oil has expired. When the approximation line changes from the first inclination to the second inclination, on the other hand, it can be judged that the oil reaches about one half of its service life.

The operation of the warning device 7 will be described below with reference to FIG. 2.

The microcomputer 12 stores the threshold value $V_1$ preset as described above. The microcomputer 12 samples the output of the pH sensor 11 at a regular interval of time, and goes on to calculate an approximation line by correlating the output to the mileage input from the meter of the panel 4. This approximation line, as described above, follows a relatively gentle upward curve having substantially the same inclination (first inclination) for some time after the vehicle starts to run. During this period (area A in FIG. 2), no information is displayed on the display unit 41 of the microcomputer 12.

When the mileage increases to some extent, the output of the pH sensor 11 exceeds the prevailing inclination (first inclination) of the approximation line, i.e., rises over a value estimated by the approximation line of the first inclination. The fact that the output of the pH sensor 11 has begun to exceed the first inclination is detected by the microcomputer 12 from the fact that the output of the pH sensor 11 has risen beyond a predetermined range of variation from the estimated value based on the assumption that the approximation line remains the first inclination (one-dot chain line in FIG. 2), so that the microcomputer 12 judges that the approximation line has changed from the first inclination to the second inclination (i.e., it has entered the area B in FIG. 2). Then, the microcomputer 12 calculates the second inclination and, based on the second inclination, the output of the pH sensor 11, the threshold value $V_1$, etc., then calculates the distance remaining to be covered before expiry of the oil service life and displays it as a warning on the display unit 41. Also, since the change from the first inclination to second inclination indicates the fact that the mileage has reached about one half of the whole oil service life, a warning of that fact may be given at that particular time.

Further, when the output of the pH sensor 11 reaches the threshold value $V_1$, the microcomputer 12 judges that the oil has reached the end point of its service life, and causes the display unit 41 to display a warning that the oil has reached the end point of its service life and the oil should be changed. On the other hand, after the oil has passed over its life end point, the microcomputer 12 causes the display unit 41 to continuously display or blink a warning that the oil must be changed. In this case, a warning that the oil should be changed may be displayed first of all at the time of starting the engine.

After that, the output of the pH sensor 11 falls below the line of the second inclination and substantially comes to be in a stable state. This stable state is detected by the microcomputer 12 from the fact that the output of the pH sensor 11 has fallen beyond a predetermined range of variation from the estimated value based on the assumption that the approximation line remains the second inclination (two-dot chain line in FIG. 2). The microcomputer 12 thus judges that the approximation line has changed from the second inclination to the third inclination (i.e., it has entered the area C in FIG. 2). As a result, the microcomputer 12 judges that the oil has passed its service life and causes the display unit 41 to emphatically display a warning that the oil must be changed, either by blinking at short intervals or with a high brightness.

In the case where the output of the pH sensor 11 fails to increase as usual due to a leakage or the like, the output of the pH sensor 11 may not reach the threshold value $V_1$. Even in such a case, when the oil passes over its service life, the output of the pH sensor 11 falls below the line of the second inclination and comes to be in a stable state. Therefore, upon detection of this stable state, the microcomputer 12 causes the display unit 41 to emphatically display a warning that the oil should be changed.

As described above, since the detection device 1 determines the arrival at the end point of the oil service life based on the output characteristic of the pH sensor 12, it can detect the arrival at the end point more accurately. Also, it can detect that about one half of the oil service life has been consumed or the service life has expired. Further, even in the case where the output of the pH sensor 12 fails to increase as usual, due to a leakage or the like, the expiry of the service life can be detected. Since the warning device 7 gives a warning of the deterioration of the oil as detected by the detection device 1, the vehicle user who has received the warning can take a protective measure, for example, by changing of the oil, in response to the warning.

The warning can be given by displaying characters or turning on a light. The warning is not necessarily displayed on the display unit 41 of the panel 4 but can be displayed on a monitor 5 which can be connected to the detection device 1 as shown in FIG. 1. In such a case, the monitor 5 functions as warning means. As another alternative, a voice output unit may be connected to the detection device 1 so that the audio warning can be given with the displaying of characters or the lighting of an alarm light. In this case, the voice output unit also functions as warning means.

Further, in the area A in FIG. 2, the microcomputer 12 may detect (estimate) the oil deterioration indirectly for giving a warning by adding up the engine revolution and additionally considering the effect of the oil temperature change on the oil deterioration. Furthermore, the distance remaining to be covered before expiry of the oil service life may be calculated and displayed based on the indirect detection (estimation) described above. In this way, even before the change to the second inclination, the vehicle user can be warned of the oil deterioration.

The configuration described above is modifiable without departing from the scope and spirit of the invention.

A second embodiment of the present invention will be also described below with reference to the drawings. The change in the change rate of the output from the pH sensor 11 is detected, in the first embodiment, based on the change in the inclination of the approximation line of the output from the pH sensor. On the other hand, it is detected, in this second embodiment, based on a change in an inclination of a vector (i.e., an angle formed between a sense of the vector and a positive direction of the lateral axis) in a line plot of the output from pH sensor 11 with respect to a total driving mileage or time. This is the reason why, in the case of using an approximation line, as this approximation line is calculated based on a series of data obtained at regular intervals, all of these data must be stored in memory in order to obtain an exact approximation line, resulting in a requirement for a high-capacity memory and consequently in an increased cost. In the above description, the term "the change rate of the output from the pH sensor" indicates a change in the output from the pH sensor per unit of driving mileage or driving time. As a construction in the hardware of the second embodiment is similar to that of the first embodiment, the like reference numerals indicate the like components in the following description.

In the second embodiment, the pH sensor 11 uses zinc and oxidized stainless steel SUS 304 for its electrode materials.

Figure 3:
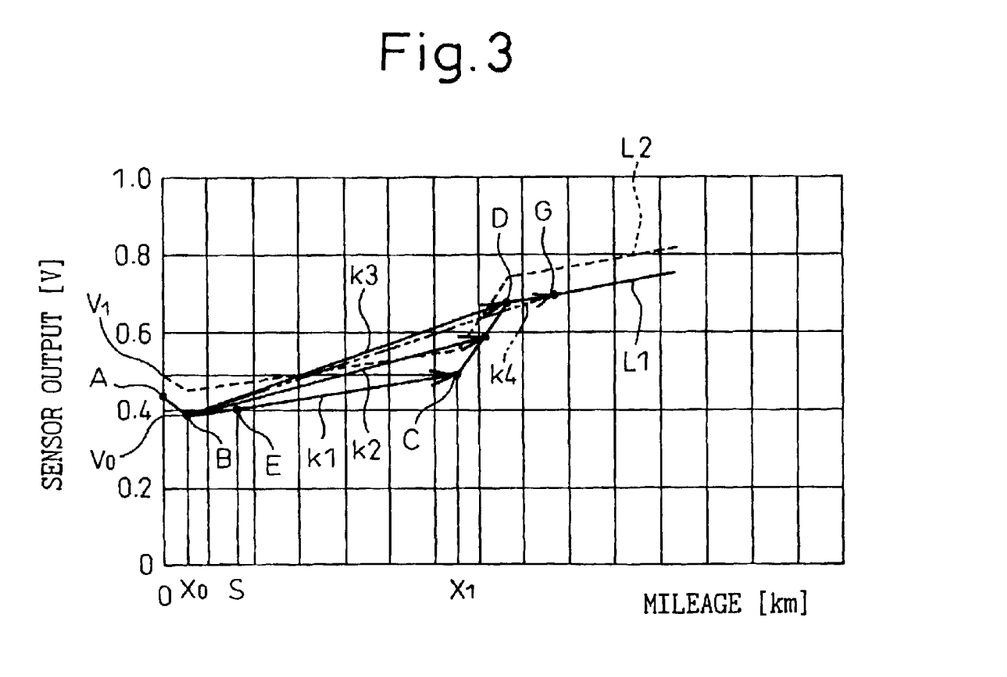
FIG. 3 is a line plot showing a change in the output from the pH sensor corresponding to the driving mileage and vectors from a point B to respective output points.

A point A is defined as a moment when the engine oil is exchanged in whole amounts, and a point B is defined as a moment when the deterioration of the oil begins to take place and the sensor output begins to increase.

After the point B is determined, the detection device 1 sequentially calculates a series of inclinations of a vector starting from the point B and ending at respective points on the coordinates having the mileage at that moment and the corresponding output from the pH sensor at the regular mileage interval s (e.g., 500 km), and stores them. The detection device 1 leaves in the memory only those data of the vector inclinations obtained at the regular mileage interval s within a predetermined range of driving mileage from that moment, and deletes the preceding data of vector inclinations before the predetermined range. Therefore, only those data within the predetermined range of the driving mileage are stored thereby to make it possible to reduce a required amount of memory. The mileage and the sensor output at a point C are denoted by $x_1$ and $V_1$, respectively.

The detection device 1 then checks a change in the inclination of the vector. The sensor output changes at a relatively small and substantially constant rate (called a first change rate) from the point B to the point C in FIG. 3. Therefore, the inclination of the vector remains substantially constant as represented by k1 in FIG. 3. After having passed over the point C, the sensor output changes at a rate greater than the first change rate (called a second change rate). Therefore, the inclination of the vector increases as represented by k2 and k3 in FIG. 3. Then, after passing over the point D, the sensor output changes at a rate smaller than the second change rate (called a third change rate). Therefore, the inclination of the vector decreases as represented by k4 in FIG. 3. It may be presumed that such a change in the change rate of the sensor output results from the combination of electrode materials which are the oxidized SUS and zinc, and from the progressing degree of deterioration of the oil. Upon detecting the fact that the inclination of the vector changes from the increasing condition to the decreasing condition, the device 1 judges that the service life of the oil has expired and gives a warning. The fact that the service life of the oil has expired includes a fact that the oil has reached the end point of its service point and that it has passed the end point of its service life.

The output from the pH sensor 11 substantially consistently continues to increase until it comes to be in a substantially stable state after having passed the point B. Therefore, the change rate referred to here can be replaced by the words "increase rate". More specifically, the sensor output increases at a relatively small first increase rate from the point B up to the point C, sharply increases at a second increase rate larger than the first increase rate from the point C up to the point D, increases at a third increase rate smaller than the second increase rate after the point D and, then, comes to be in a stable state. Therefore, the inclination of a vector starting from the point B and ending at a point on a coordinate having a present driving mileage and a present corresponding sensor output also changes from a substantially constant condition into an increasing condition, and from the increasing condition to a decreasing condition.

Figure 4:
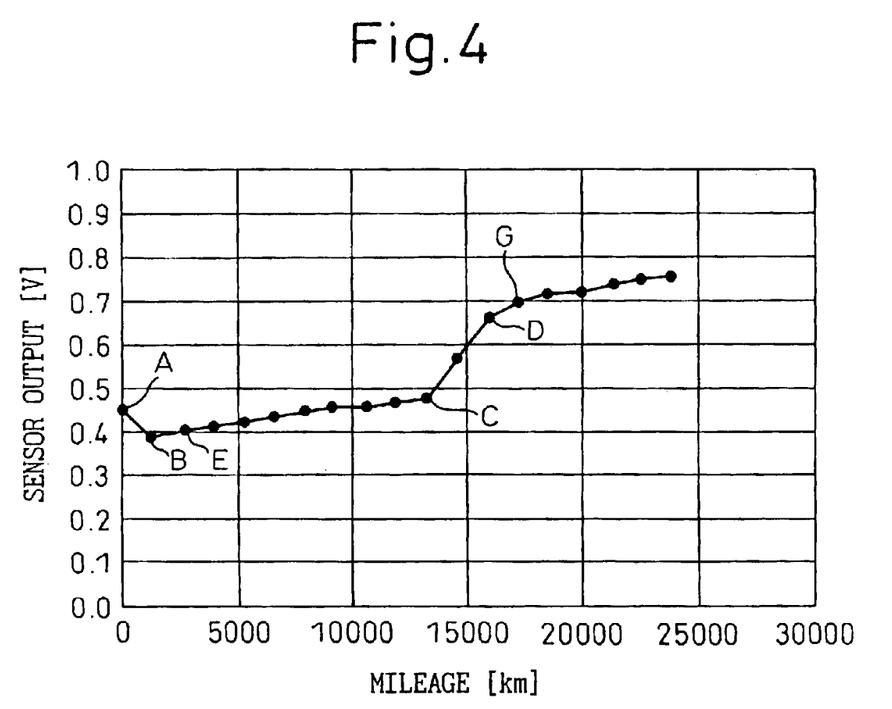
FIG. 4 is a line plot showing a relationship between the driving mileage and the corresponding output from the pH sensor.
Figure 5:
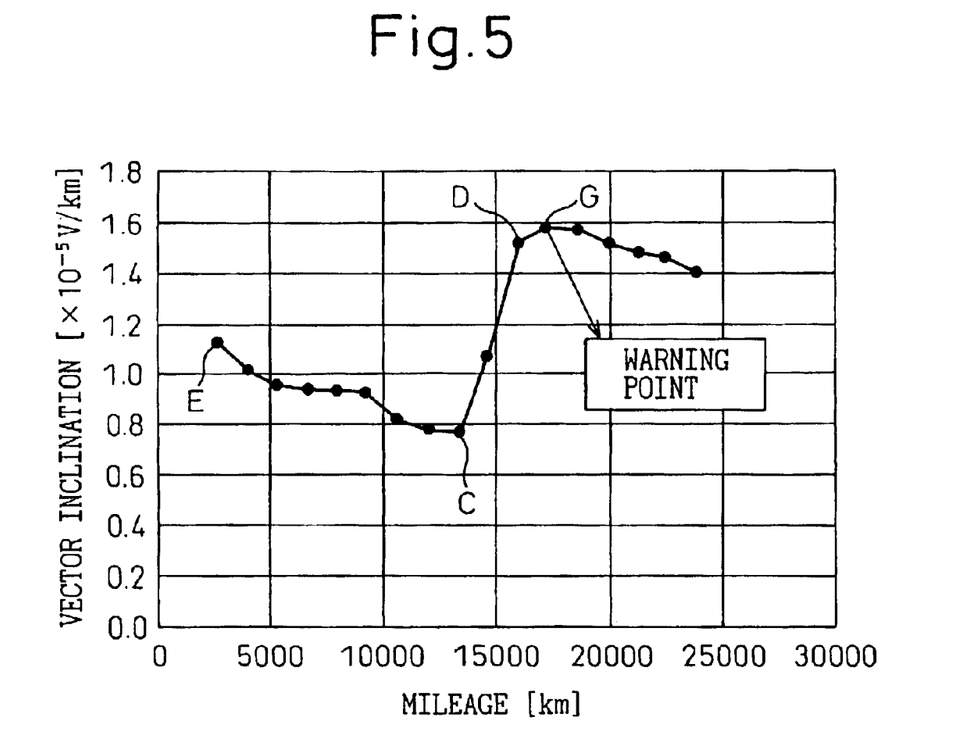
FIG. 5 is a line plot showing a relationship between the driving mileage and an inclination of a vector from the point B to the respective point of FIG. 4 as calculated based on the data of FIG. 4.

FIG. 4 is a diagram illustrating a relationship between the mileage and the sensor output in the case of actually driving a vehicle under a given condition, and FIG. 5 is a diagram illustrating a change in the inclination of the vector as calculated based upon the data of FIG. 4. It can be seen from FIG. 5 that the inclination of the vector is substantially constant or decreases from a point E to a point C, increases from the point C to a point D, and is substantially constant or decreases after the point D. Therefore, the detection device 1 gives a warning for changing the oil at a point G after the point D. Although FIG. 5 illustrates all of the calculated vector inclinations, the detection device 1, in practice, checks the change in the vector inclinations within a predetermined range of the recent driving mileage (going back to the past), as described earlier, thereby to judge the service life of the oil.

In this second embodiment, the service life of the oil is judged without using an absolute value of the sensor output. Accordingly, dispersion depending upon the sensors has no effect on the judgement of the service life of the oil, and no process is required for pre-adjustment. More specifically, even when the sensors have the same constitution using the same electrode materials, their output may follow a path as represented by, for example, the solid line L1 in FIG. 3 or may follow a path as represented by a broken line L2, depending upon the quality of the individual sensors. Therefore, if the service life is judged by presuming that the output of the sensor follows the path as represented by the solid line L1 and using an absolute value (e.g., output value corresponding to the point D), it can be judged that the service life has expired when the output follows the path as represented by the broken line L2, though the service life has not actually been expired. This can result in an incorrect judgement. In order to prevent such an incorrect judgement, a process for pre-adjustment of the sensor is necessary such as by effecting the correction depending upon the quality of the individual sensors. On the contrary, in the second embodiment, the service life is judged without using the absolute value of the sensor output but by detecting a relative change such as whether the inclination of the vector has become greater or smaller than the previous inclination. Therefore, the service life can be precisely judged without any effect of the quality of the sensors and by using the same logic circuit even when there are used the sensors having different sensor outputs in absolute values.

Further, difference in the kind of oil causes a difference in the absolute value of the sensor output but does not affect the tendency of the change in the change rate of the sensor output, i.e., the change rate of the sensor output changes from a small state to a large state and from the large state to a small state. As the detection device 1 judges the oil deterioration by monitoring a change in the change rate of the sensor output, it can precisely judge the oil deterioration even when the kind of oil is different.

Also, the second embodiment makes it possible to reduce the necessary capacity of memory, resulting in a lower cost as compared to when the approximation lines described above is used.

While in the second embodiment, the oxidized SUS and zinc are used for the electrode materials of the pH sensor, it should be noted that the invention is not intended to be limited to this combination only.

Further, the predetermined range S of the driving mileage or the value s may be varied. Moreover, the oil deterioration may be judged by monitoring a change in a change rate of the sensor output corresponding to driving time instead of the driving mileage.

What is claimed is:

1. A method of detecting a deterioration of vehicle oil, said method comprising steps of:
   measuring an acidity or basicity of the vehicle oil using a pH sensor generating an output in response to the degree of the acidity or basicity of the vehicle oil;
   monitoring a change in a change rate of the output from said pH sensor with one of an increasing driving mileage or driving time of a vehicle;
   detecting the fact that the output from said pH sensor, after changing from a changing at a first change rate to a changing at a second change rate greater than said first change rate, changes from the changing at said second change rate to a changing at a third change rate smaller than said second change rate; and
   judging that the service life of the vehicle oil has expired when the output from said pH sensor changes at said third change rate to detect the deterioration of the vehicle oil.

2. The method according to claim 1, wherein said monitoring step includes a step of using an approximation line approximating the output from said pH sensor with respect to the mileage of said vehicle, and
   wherein said method comprises a step of detecting the deterioration of the vehicle oil, based on the fact that the approximation line has a tendency to change from a first inclination to a second inclination lager than said first inclination and from said second inclination to a third inclination smaller than said second inclination, with the increasing mileage of said vehicle.

3. The method according to claim 2, wherein said judging step includes steps of predetermining a threshold value existing between a portion of said second inclination and a portion of said third inclination in said approximation line, and detecting that the vehicle oil has reached the end point of the service life thereof based on the predetermined threshold value.

4. The method according to claim 3, wherein said judging step includes steps of predetermining a threshold value existing between a portion of said second inclination and a portion of said third inclination in said approximation line, and detecting that the vehicle oil has reached the end point of the service life thereof based on the predetermined threshold value.

5. The method according to claim 2, further comprises a step of judging that the vehicle oil has reached about one half of the service life thereof when said approximation line has come to have said second inclination.

6. The method according to claim 5, wherein said judging step includes steps of predetermining a threshold value existing between a portion of said second inclination and a portion of said third inclination in said approximation line, and detecting that the vehicle oil has reached the end point of the service life thereof based on the predetermined threshold value.

7. The method according to claim 2, wherein said judging step comprises a step of judging that the vehicle oil has passed over the end point of the service life when said approximation line has come to have said third inclination.

8. The method according to claim 7, wherein said judging step includes steps of predetermining a threshold value existing between a portion of said second inclination and a portion of said third inclination in said approximation line, and detecting that the vehicle oil has reached the end point of the service life thereof based on the predetermined threshold value.

9. A method of warning a vehicle user of the deterioration of the vehicle oil detected by the method according to claim 2.

10. A method of warning a vehicle user of the deterioration of the vehicle oil detected by the method according to claim 1.

11. The method according to claim 1, wherein said monitoring step includes steps of defining a plane with the driving mileage or driving time as an abscissa thereof and with the output of said pH sensor as an ordinate thereof perpendicular to the abscissa, and using a vector on said plane starting from a point on a coordinate having a driving mileage or driving time $x_0$ and a corresponding output $V_0$ from said pH sensor and ending at a point on a coordinate having a driving mileage or driving time $x_1$ greater than $x_0$ and a corresponding output $V_1$ from said pH sensor; and
   wherein said method comprises a step of detecting the deterioration based on the fact that the inclination of said vector has a tendency to change from a substantially constant or decreasing condition to an increasing condition and from the increasing condition to a substantially constant or decreasing condition, with the increasing driving mileage or driving time.

12. The method according to claim 11, wherein the output from said pH sensor at first decreases in a predetermined range S of the driving mileage or driving time from an oil exchange and thereafter increases with the increasing driving mileage or driving time; and
   wherein a point of a minimum output from said pH sensor within the predetermined range S of the driving mileage or driving time from the oil exchange is defined as said starting point.

13. The method according to claim 12, wherein said judging step includes steps of predetermining a threshold value existing between a portion of said second inclination and a portion of said third inclination in said approximation line, and detecting that the vehicle oil has reached the end point of the service life thereof based on the predetermined threshold value.

14. The method according to claim 11, wherein said step of detecting the deterioration of the vehicle oil is performed based on a change in the inclinations of said vectors obtained by sampling the outputs of said pH sensor at a regular interval of the driving mileage or driving time in a predetermined range of a recent driving mileage or driving time.

15. The method according to claim 14, wherein said judging step includes steps of predetermining a threshold value existing between a portion of said second inclination and a portion of said third inclination in said approximation line, and detecting that the vehicle oil has reached the end point of the service life thereof based on the predetermined threshold value.

16. The method according to claim 11, wherein said judging step includes steps of predetermining a threshold value existing between a portion of said second inclination and a portion of said third inclination in said approximation line, and detecting that the vehicle oil has reached the end point of the service life thereof based on the predetermined threshold value.

17. A device for detecting a deterioration of a vehicle oil, said device comprising:
- a pH sensor mounted on an oil pan of said vehicle for generating an output in response to the degree of the acidity or basicity of the vehicle oil; and
- means connected to said pH sensor for judging the deterioration of the vehicle oil, based on a driving mileage input to said pH sensor and the corresponding output from said pH sensor;
- wherein said judging means detects the fact that the output from said pH sensor, after changing from a changing at a first change rate to a changing at a second change rate greater than said first change rate, changes from the changing at said second change rate to a changing at a third change rate smaller than said second change rate, and judges that the service life of the vehicle oil has expired when the output from said pH sensor comes to change at said third change rate.

18. The device according to claim 17, wherein said judging means detects the deterioration of the vehicle oil, based on the fact that an approximation line approximating the output from said pH sensor with respect to the mileage of said vehicle has a tendency to change from a first inclination to a second inclination larger than said first inclination and from said second inclination to a third inclination smaller than said second inclination, with the increasing mileage of said vehicle.

19. The device according to claim 18, wherein said judging means detects that the vehicle oil has reached the end point of the service life thereof, based on a predetermined threshold value existing between a portion of said second inclination and a portion of said third inclination in said approximation line.

20. An oil deterioration warning device, comprising a device for detecting a deterioration of a vehicle oil according to claim 19; and means for warning a vehicle user of the deterioration of the vehicle oil detected by said device.

21. The device according to claim 18, wherein said judging means detects the changing of said approximation line to said second inclination, based on the output from said pH sensor, and judges that the vehicle oil has reached about one half of the service life thereof when said approximation line has come to have said second inclination.

22. An oil deterioration warning device, comprising a device for detecting a deterioration of a vehicle oil according to claim 21; and means for warning a vehicle user of the deterioration of the vehicle oil detected by said device.

23. The device according to claim 18, wherein said judging means detects the changing of said approximation line to said third inclination, based on the output from said pH sensor, and judges that the vehicle oil has passed over the end point of the service life when said approximation line has come to have said third inclination.

24. An oil deterioration warning device, comprising a device for detecting a deterioration of a vehicle oil according to claim 23; and means for warning a vehicle user of the deterioration of the vehicle oil detected by said device.

25. An oil deterioration warning device, comprising a device for detecting a deterioration of a vehicle oil according to claim 18; and means for warning a vehicle user of the deterioration of the vehicle oil detected by said device.

26. A oil deterioration warning device, comprising a device for detecting a deterioration of a vehicle oil according to claim 17; and means for warning a vehicle user of the deterioration of the vehicle oil detected by said device.

* * * * *